US00PP33431P2

(12) United States Plant Patent
Burton

(10) Patent No.: US PP33,431 P2
(45) Date of Patent: Aug. 31, 2021

(54) ***LOMANDRA* PLANT NAMED 'ARCTIC FROST'**

(50) Latin Name: *Lomandra longifolia*
Varietal Denomination: Arctic Frost

(71) Applicant: Lifetech Laboratories Limited, Auckland (NZ)

(72) Inventor: Graeme John Burton, Ohaupo (NZ)

(73) Assignee: Lifetech Laboratories Limited, Auckland (NZ)

( * ) Notice: Subject to any disclaimer, the term of this patent is extended or adjusted under 35 U.S.C. 154(b) by 0 days.

(21) Appl. No.: 17/073,915

(22) Filed: Oct. 19, 2020

(51) Int. Cl.
*A01H 5/02* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 6/12; A01H 5/02; A01H 5/12
See application file for complete search history.

*Primary Examiner* — Keith O. Robinson
(74) *Attorney, Agent, or Firm* — Penny J. Aguirre

(57) ABSTRACT

A new cultivar of *Lomandra longifolia* plant named 'Arctic Frost' that is characterized by its foliage that is dark green in color (primary color) with white longitudinal variegation that is distinctive, contrasting and vivid and its tips on the ends of the leaves that are white in color.

2 Drawing Sheets

Botanical classification: *Lomandra longifolia.*
Varietal denomination: 'Arctic Frost'.

BACKGROUND OF THE INVENTION

The present invention relates to a new and distinct cultivar of *Lomandra longifolia* and will be referred to hereafter by its cultivar name, 'Arctic Frost'. 'Arctic Frost' is a new cultivar of perennial ornamental grass grown for container and landscape use.

The Inventor discovered the new cultivar April of 2015 as a naturally occurring chimeral mutation of *Lomandra longifolia* 'LM400' (U.S. Plant Pat. No. 15,583) that was growing in a container in his nursery in Hamilton, New Zealand.

Asexual propagation of the new cultivar was first accomplished by division under the direction of the Inventor in April of 2015 in Hamilton, New Zealand. Asexual propagation by tissue culture using meristem tissue and division have determined that the characteristics are stable and are reproduced true to type in successive generations.

SUMMARY OF THE INVENTION

The following traits have been repeatedly observed and represent the characteristics of the new cultivar. These attributes in combination distinguish 'Arctic Frost' as a distinct cultivar of *Lomandra.*

1. 'Arctic Frost' exhibits foliage that is dark green in color (primary color) with white longitudinal variegation that is distinctive, contrasting and vivid.
2. 'Arctic Frost' exhibits tips on the ends of the leaves that are white in color.

The parent plant of 'Arctic Frost', 'LM400', is similar to 'Arctic Frost' in leaf form and leaf length but differs from 'Arctic Frost' in having blue-tinted green foliage that is not variegated. 'Arctic Frost' can be most closely compared to *Lomandra longifolia* 'Roma 13' (U.S. Plant Pat. No. 25,962). 'Roma 13' is similar to 'Arctic Frost' in having variegated foliage. 'Roma 13' differs from 'Arctic Frost' in having green and yellow variegated leaves with the yellow in color with the yellow variegation more prevelant (less green) than the white variegation of 'Arctic Frost'.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Provender Nurseries, Waitrose Garden, RHS Gardening, ebay, Crocus, 4utoday, PP&L, Seiont Nurseries, and Gardenzia.

BRIEF DESCRIPTION OF THE DRAWINGS

The accompanying colored photographs illustrate the overall appearance and distinct characteristics of a 10-month-old plant the new *Lomandra* as grown outdoors in a 1-gallon container in Waltsonville, Calif.

The photograph in FIG. 1 provides a side view of the plant habit and appearance of 'Arctic Frost'.

Figure 1:
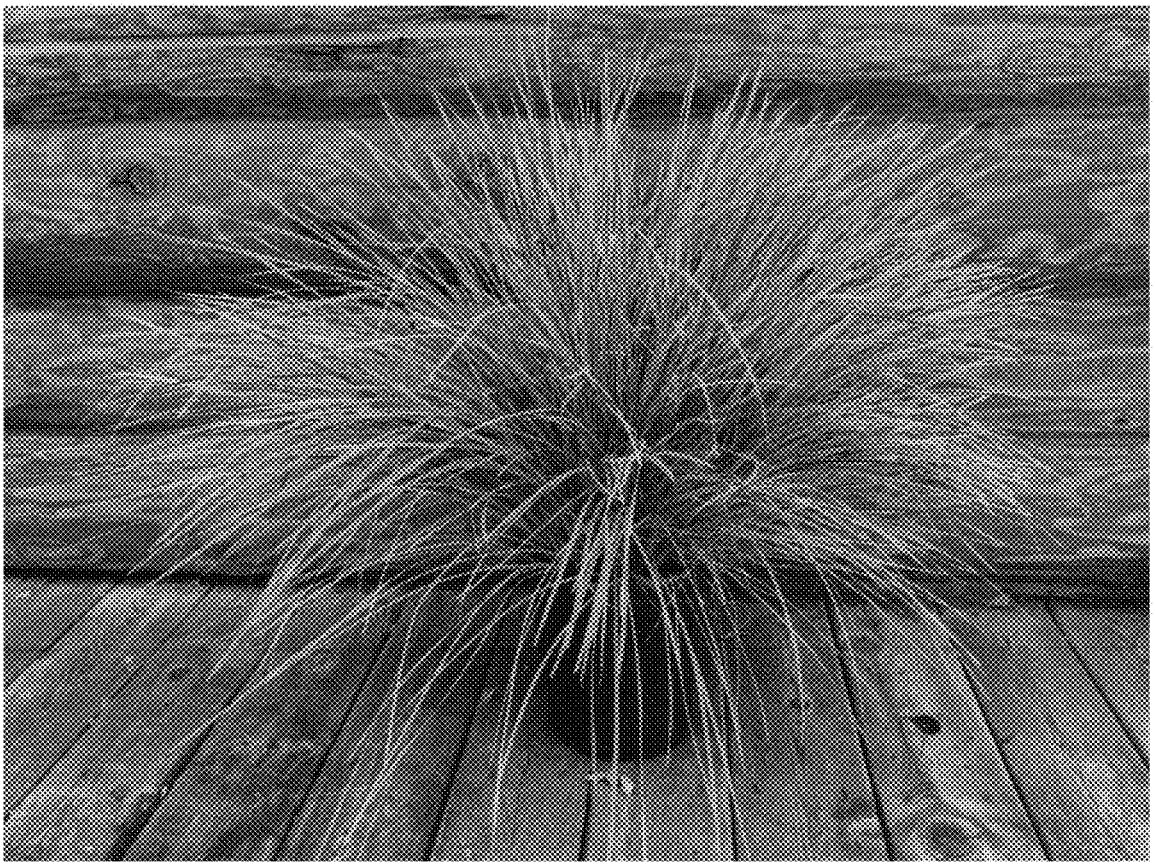
Figure 2:
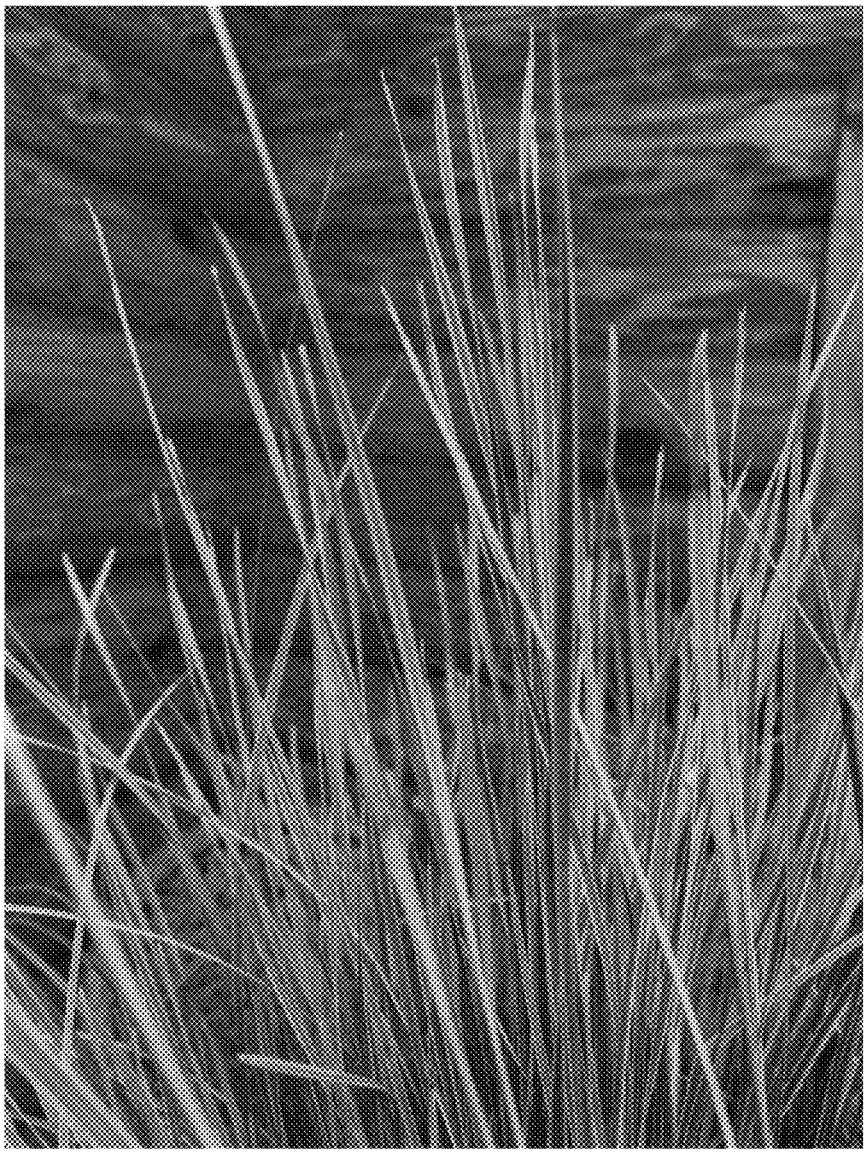

The photograph in FIG. 2 provides a close-up view of the foliage of 'Arctic Frost'.

The colors in the photographs may differ slightly from the color values cited in the detailed botanical description, which accurately describe the colors of the new *Lomandra.*

DETAILED BOTANICAL DESCRIPTION

The following is a detailed description of 10-month-old plants the new *Lomandra* as grown outdoors in 1-gallon containers in Waltsonville, Calif. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type*.—Evergreen perennial grass.

*Plant habit*.—Compact, tussock, vertical to arching narrow leaves.

*Height and spread*.—60 cm in height and 95 cm in diameter.

*Hardiness*.—At least in U.S.D.A. Zones 8 to 10.

*Diseases and pests*.—No susceptibility or resistance to pests and diseases has been observed.

*Root description*.—Short, stout rhizomes; average of 5 cm in length with a smooth texture, fine, fibrous roots that are moderately branched, 155C in color.

*Propagation*.—Tissue culture and division.

*Root development*.—Time required for root initiation is an average of 4 weeks in tissue culture, time required to produce a young plant from rooted cutting is 6 months in spring and up to 1 year during other seasons.

*Growth rate*.—Moderate.

Foliage description:

*Leaf shape*.—Linear.

*Leaf division*.—Simple.

*Leaf base*.—Sheathing.

*Leaf apex*.—Long acuminate.

*Leaf aspect*.—Center leaves vertical, surrounding leaves initially emerge upright, then cascade outward and finally arching downward.

*Leaf venation*.—Linear, upper and lower surface N189C.

*Leaf margins*.—Entire, smooth.

*Leaf size*.—Average of 65 cm in length and 4 mm in width.

*Leaf number*.—Average of 14 leaves per shoot.

*Leaf arrangement*.—Opposite.

*Leaf strength*.—Bendable and very strong.

*Leaf surface*.—Both surfaces slightly glossy and becoming mostly matte as the leaves mature.

*Leaf color*.—Young inner and outer surfaces; variagated, base and center 144A, margins NN155D, tips NN155D, mature inner and outer surfaces; variagated, base and center N189A and 139A, margins are very thin NN155D, tips NN155D.

*Leave sheathes*.—Average of 5 cm in length, 1 cm in width, surface color matches leaf color description of base, margins of sheathes are transparent, thin and paper-like, a blend of 191D and NN155D in color.

Flower description:

*General description*.—Panicle of clusters of male flowers, not conspicous as the blooms are held within the foliage.

*Inflorescence size*.—Panicle 7 to 20 cm in height and up to 2 cm in width, clusters; an average of 1.9 mm in depth and 2.5 mm in diameter.

*Flower quantity per inflorescence*.—Average of 15 clusters per panicle, 5 flowers per cluster.

*Lastingness of inflorescence*.—Flowers last an average of 10 days before drying, persistent.

*Flowering season*.—In spring and re-blooming in summer in New Zealand.

*Fragrance*.—Moderate, typical of species.

*Flower buds*.—Oval in shape, average of 2 mm in length, 183D in color.

*Flower size*.—Average of 3.5 mm in length and 1.57 mm in width.

*Flower shape*.—Closed campanulate.

*Flower color*.—A blend of 162D, 6D, and 146D on inner and outer surface of tepals, fading to 162C when dried.

*Bracts*.—Average of 4 mm in length (including spike), a blend of 199C an 183D in color with spike 162D, triangular in shape, truncate base, apex is a spike an average of 2 mm in length but can reach 6 mm in length, smooth surfaces.

*Peduncle*.—Rachis; up to 20 cm in length and 1 mm in diameter, upright strong, secondary peduncles; an average of 2 cm in length an 0.75 mm in width, held at a about 20° to vertical, color 137C in color becoming 162D when dried, surfaces smooth.

*Pedicel*.—None, flowers sessile to peduncle.

Reproductive organs:

*Gynoecium*.—None, male flowers only.

*Androecium*.—6 stamens, average of 0.9 mm in length with anther 8C in color, pollen not observed.

*Fruits and seeds*.—Male flowers, no seed is produced.

It is claimed:

1. A new and distinct cultivar of *Lomandra* plant named 'Arctic Frost' as herein illustrated and described.

* * * * *